United States Patent
Krohn et al.

(10) Patent No.: US 12,329,839 B2
(45) Date of Patent: *Jun. 17, 2025

(54) ACTIVE SUBSTANCE COMPOSITION FOR PROTECTING ARTIFICIALLY COLOURED HAIR

(71) Applicant: Henkel AG & Co. KGaA, Duesseldorf (DE)

(72) Inventors: Rene Krohn, Norderstedt (DE); Erik Schulze Zur Wiesche, Bielefeld (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 1047 days.

This patent is subject to a terminal disclaimer.

(21) Appl. No.: 17/289,587

(22) PCT Filed: Oct. 31, 2019

(86) PCT No.: PCT/EP2019/079786
§ 371 (c)(1),
(2) Date: Apr. 28, 2021

(87) PCT Pub. No.: WO2020/089371
PCT Pub. Date: May 7, 2020

(65) Prior Publication Data
US 2022/0008312 A1    Jan. 13, 2022

(30) Foreign Application Priority Data
Oct. 31, 2018   (DE) .................... 10 2018 127 300.2

(51) Int. Cl.
*A61K 8/58*   (2006.01)
*A61K 8/81*   (2006.01)
*A61Q 5/00*   (2006.01)

(52) U.S. Cl.
CPC ............ *A61K 8/585* (2013.01); *A61K 8/8147* (2013.01); *A61K 8/8158* (2013.01); *A61Q 5/004* (2013.01)

(58) Field of Classification Search
CPC ....................................................... A61K 8/585
See application file for complete search history.

(56) References Cited

FOREIGN PATENT DOCUMENTS

| DE | 102009027678 A1 | 5/2010 |
| DE | 102009044920 A1 | 4/2011 |
| EP | 1767187 A2 | 3/2007 |
| EP | 2347795 A2 | 7/2011 |
| WO | 2016091456 A1 | 6/2016 |
| WO | 2017102856 A1 | 6/2017 |
| WO | 2017102857 A1 | 6/2017 |

OTHER PUBLICATIONS

EPO, International Search Report issued in International Application No. PCT/EP2019/079786, dated Jan. 24, 2020.
Anonymous: "Anti-Dryness Cleansing Cream", Mintel, Nov. 2008, XP055657045, Database accession No. 1009536, www.gnpd.com.
Woodruff: "Hair care—Crowning glory", Nov. 2012, XP055656728, URL:https://www.manufacturingchemist.com/technical/article_page/ Hair_care Crowning_glory/82206.

*Primary Examiner* — Benjamin J Packard
(74) *Attorney, Agent, or Firm* — Lorenz & Kopf, LLP

(57) ABSTRACT

The present disclosure relates to an active ingredient composition for shape change and surface modification of human hair: The present disclosure especially relates to a cosmetic product for the treatment of a keratinous material, comprising a) at least one organic silicon compound and b) at least one polyacrylate copolymer, wherein the cosmetic product is especially suitable for the treatment of colored hair.

20 Claims, No Drawings

ACTIVE SUBSTANCE COMPOSITION FOR PROTECTING ARTIFICIALLY COLOURED HAIR

CROSS-REFERENCE TO RELATED APPLICATION

This application is a U.S. National-Stage entry under 35 U.S.C. § 371 based on International Application No. PCT/EP2019/079786, filed Oct. 31, 2019, which was published under PCT Article 21(2) and which claims priority to German Application No. 10 2018 127 300.2, filed Oct. 31, 2018, which are all hereby incorporated in their entirety by reference.

TECHNICAL FIELD

The present disclosure relates to cosmetic products for the treatment of a keratinous material, wherein the product comprises an organic silicon compound and comprises at least one polyacrylate, as well as the use of the cosmetic product.

BACKGROUND

The cosmetic treatment of skin and hair is an important component of the human body care. Human hair is, thus, treated in multiple ways with hair cosmetic preparations. This covers, for example, cleaning of the hair with shampoos, the care and regeneration with rinsing and cures such as bleaching, coloring and shaping of the hair using dyes, tints, waving agents, and styling preparations. Agents for changing or shading the color of the head hair play a special role in this case. Not considering the blonding agents that effect an oxidative lightening of the hair by destroying natural hair pigments, there are mainly three important types of hair dyes in the field of hair coloring. So-called oxidation dyes are used for permanent, intensive coloring with corresponding fastness properties. The oxidation dyes are used for permanent, intensive dyeing with corresponding fastness features. Such dyes usually contain oxidation dye precursors, so-called developer components and coupler components.

If the dyes formed or used in the course of the color formation have distinctly different fastness properties (e.g. UV stability, perspiration fastness, washing fastness etc.), in the course of time it can lead to a discernible and therefore undesirable color shift. Frequent washing and other care treatments can also cause color shifts. This phenomenon appears strongly if the hair style shows hair or hair zones of differing degrees of damage. An example of this is long hair, wherein the hair tips exposed to all possible environmental influences over a long period are generally more damaged than the relatively freshly regrown hair zones.

Dyes or toning agents that contain what are called direct acting dyes as coloring components are usually used for temporary coloring. Direct-acting dyes are dye molecules that draw directly onto the hair and do not require an oxidative process to form the color. These colorings are generally distinctly more sensitive to shampooing than oxidative coloring is, so in such cases a much unwanted change in the shading, or even a visible 'discoloration', takes place must faster.

In another commonly used dyeing process, precursors of Melanin, the natural hair dye, are applied to the hair; they go on to form dyes which are analogous to natural ones, as part of the oxidative processes. In such methods, 5,6-dihydroxyindolin, for example, is used as a dye precursor. On using agents with 5,6-dihydroxyindolin, especially multiple times, it is possible to return the natural color in humans with graying hair. The coloring can in that case take place with air oxygen as the sole oxidation agent, so no other oxidation agent need be resorted to.

Multiple problems arise in all hair coloring. For one thing, an undesired coloring of the skin areas can occur on rinsing off the hair dye. This effect can also cause the dye to post-color lighter highlights on washing off, or the dye can color the lighter base hair from the darker highlights on washing off. Washing off of dyes generally entails the disadvantage that the originally desired color changes. Especially hair dyes with red or blue tones have a short dwell time in the hair, so washing them off leads to unwanted colors. This problem is also countered by color protection products.

Secondly, all chemical stresses obstruct coloring processes. External stressing of the hair due to chemical materials from a variety of different sources poses challenges for the development of cosmetic care products. Air and water pollution adversely affects skin and hair. The most important air pollutants include polycyclic aromatic hydrocarbons, volatile organic compounds, nitrogen oxide (NOx), particles and cigarette smoke. The presence of other air pollutants and to UV radiation can reinforce the effect of various air pollutants.

Furthermore, frequently changing customer requests regarding a certain finish of the hair are linked to a recurrent chemical stress on the hair. For example, hair dyes stress the hair, due to which, an intensive care may be necessary.

Organic compounds of silica from the group of silanes are described in the state of the art, which comprise at least one hydroxy group and/or hydrolysable group. Due to the presence of hydroxy groups and/or hydrolysable groups, silanes are reactive substances that hydrolyze or oligomerize or polymerize in the presence of water. When using on a keratinous material, oligomerization or polymerization of the silanes initiated by the presence of water eventually causes the formation of a film that can provide protection.

BRIEF SUMMARY Cosmetic products for the treatment of keratinous material are provided, as well as methods of using the same. In an exemplary embodiment, a cosmetic product for the treatment of keratinous material includes an organic silicon compound and a polyacrylate copolymer. The organic silicon compound has one to three silicon atoms, and the polyacrylate copolymer is formed from the monomers acrylic acid and acrylamidopropyltrimonium chloride.

A method of using a cosmetic product for the treatment of keratinous material is provided in another embodiment. The method includes applying the cosmetic product to the keratinous material, where the cosmetic product includes an organic silicon compound and a polyacrylate copolymer. The organic silicon compound has one to three silicon atoms, and the polyacrylate copolymer is formed from the monomers acrylic acid and acrylamidopropyltrimonium chloride.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task underlying the present disclosure includes the provision of a cosmetic product that makes it possible to shape hair well and improves the structure and protects against chemical stress.

This objective is achieved by employing a cosmetic product for treating a keratinous material, comprising
  a) at least one organic silicon compound that contains one to three silicon atoms and
  b) at least one polyacrylate copolymer that is formed from the monomers acrylic acid and acrylamidopropyltrimonium chloride.

Keratinous material includes hair, skin, and nails (such as fingernails and/or toenails). Wool, furs and feathers also fall under the definition of keratinous material.

Preferably, a keratinous material is understood to be human hair, human skin and human nails, especially fingernails and toenails. Especially preferably, keratinous material is understood to be human hair, head and beard hair in particular.

As the first ingredient essential for the present disclosure, the cosmetic product for the treatment of a keratinous material contains at least one organic silicon compound that contains one to three silicon atoms. Preferred organic silicon compounds are selected from silanes with one, two or three silicon atoms, where the organic silicon compound comprises one or more hydroxyl groups and/or hydrolyzable groups per molecule.

Organic silicon compounds, alternatively called organosilicon compounds, are compounds which either have a direct silicon-carbon bond (Si—C) or in which the carbon is bonded to the silicon atom via an oxygen, nitrogen or sulfur atom. The organic silicon compounds are compounds containing one to three silicon atoms. Organic silicon compounds preferably contain one or two silicon atoms.

According to IUPAC rules, the term silane stands for a group of chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

Composition (a) contains at least one organic silicon compound selected from silanes having one, two or three silicon atoms, wherein the organic silicon compound comprises one or more hydroxyl groups or hydrolyzable groups per molecule.

As part of a particularly preferred embodiment, the product for the treatment of a keratinous material features at least one organic silicon compound, selected from silanes having one, two or three silicon atoms, the organic silicon compound further comprising one or more basic groups and one or more hydroxyl groups or hydrolyzable groups per molecule.

This basic group can be, for example, an amino group, an alkylamino group or a dialkylamino group, which is preferably connected to a silicon atom via a linker. The basic group is preferably an amino group, a $C_1$-$C_6$ alkylamino group or a di($C_1$-$C_6$)alkylamino group.

The hydrolyzable group(s) is (are) preferably a $C_1$-$C_6$ alkoxy group, especially an ethoxy group or a methoxy group. It is preferred when the hydrolyzable group is directly bonded to the silicon atom. For example, if the hydrolyzable group is an ethoxy group, the organic silicon compound preferably contains a structural unit R'R"R'"Si—O—$CH_2$—$CH_3$. The residues R', R" and R'" represent the three remaining free valences of the silicon atom.

Particularly good results could be obtained if the product for the treatment of a keratinous material contains at least one organic silicon compound of formula (I) and/or (II).

The compounds of formulae (I) and (II) are organic silicon compounds selected from silanes having one, two or three silicon atoms, the organic silicon compound comprising one or more hydroxyl groups and/or hydrolysable groups per molecule.

In another specifically preferred embodiment, the product for the treatment of a keratinous material contains at least one organic silicon compound of formula (I) and/or (II).

$$R_1R_2N\text{-}L\text{-}Si(OR_3)_a(R_4)_b \quad (I),$$

where
$R_1$, $R_2$ both represent a hydrogen atom, and
L represents a linear, divalent $C_1$-$C_6$-alkylene group, preferably a propylene group (—$CH_2$—$CH_2$—$CH_2$—) or an ethylene group (—$CH_2$—$CH_2$—),
$R_3$, $R_4$ independently represent a methyl group or an ethyl group,
a stands for the number 3 and
b stands for the number 0,

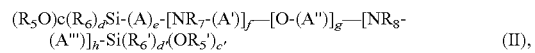

$$(R_5O)c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where
R5, R5', R5" independently represent a hydrogen atom or a $C_1$-$C_6$ alkyl group,
R6, R6' and R6" independently represent a $C_1$-$C_6$ alkyl group,
A, A', A", A'" and A"" independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

$$\text{-}(A'''')\text{-}Si(R_6'')_{d''}(OR_5'')_{c''} \quad (III),$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g and h is different from 0.

The substituents $R_1$, $R_2$, $R_3$, $R_4$, $R_5$, $R_5'$, $R_5"$, $R_6$, $R_6'$, $R_6"$, $R_7$, $R_8$, L, A', A'" and A"" in the compounds of formula (I) and (II) are explained below as examples:

Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl radicals. Examples of a $C_2$-$C_6$ alkenyl group are vinyl, allyl, but-2-enyl, but-3-enyl and isobutenyl. Preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, and the 3-aminopropyl group. The 2-aminoethyl group is particularly preferred. Examples of a linear divalent $C_1$-$C_{20}$-alkylene group include, for example, the methylene group (—$CH_2$—), the ethylene group (—$CH_2$—$CH_2$—), the propylene group (—$CH_2$—$CH_2$—$CH_2$—) and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—$CH(CH_3)$—) and (—$CH_2$—$CH(CH_3)$—$CH_2$—).

In the organic silicon compounds of the formula (I)

the radicals $R_1$ and $R_2$ independently of one another represent a hydrogen atom or a $C_1$-$C_6$ alkyl group. In particular, the radicals $R_1$ and $R_2$ both represent a hydrogen atom.

In the middle part of the organic silicon compound is the structural unit or the linker -L- which stands for a linear or branched, divalent $C_1$-$C_{20}$ alkylene group.

Preferably -L- stands for a linear, divalent $C_1$-$C_{20}$ alkylene group. Further preferably -L- stands for a linear divalent $C_1$-$C_6$ alkylene group. Particularly preferred -L stands for a methylene group ($CH_2$—), an ethylene group (—$CH_2$—$CH_2$—), a propylene group (—$CH_2$—$CH_2$—$CH_2$—) or a butylene (—$CH_2$—$CH_2$—$CH_2$—$CH_2$—). In particular, L stands for a propylene group (—$CH_2$—$CH_2$—$CH_{2[MDS1]}$—).

The organic silicon compounds of formula (I)

carry the silicon-containing grouping —$Si(OR_3)_a(R_4)_b$ at one end.

In the terminal structural unit —$Si(OR_3)_a(R_4)_b$, $R_3$ is hydrogen or $C_1$-$C_6$ alkyl group, and $R_4$ is a $C_1$-$C_6$ alkyl group. Particularly preferred, $R_3$ and $R_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

The best protection from the negative effects of water and/or air pollutants ("Anti-pollution" effect) and the best care of stressed hair could be obtained, if the features for the treatment of a keratinous material contains at least one organic silicon compound of the formula (I), in which the radicals $R_3$, $R_4$ independently represent a methyl group or an ethyl group.

Especially well-suited organic silicon compounds of the formula (I) are:

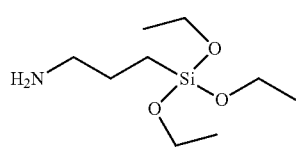

(3-Aminopropyl)triethoxysilane

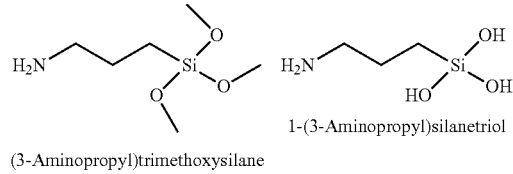

(3-Aminopropyl)trimethoxysilane

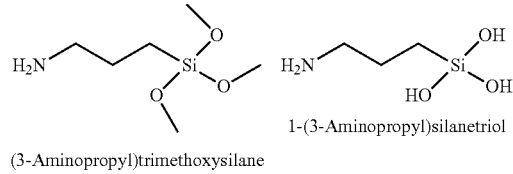

1-(3-Aminopropyl)silanetriol

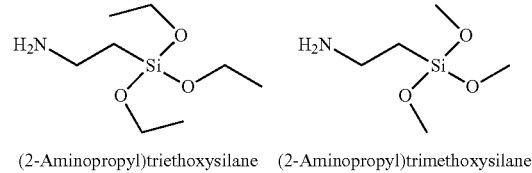

(2-Aminopropyl)triethoxysilane    (2-Aminopropyl)trimethoxysilane

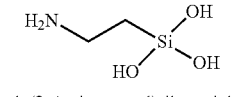

1-(2-Aminopropyl)silanetriol

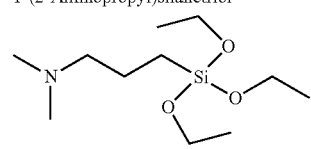

(3-Dimethylaminopropyl)triethoxysilane

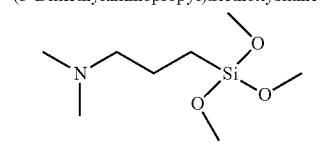

(3-Dimethylaminopropyl)trimethoxysilane

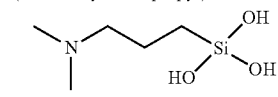

1-(3-Dimethylaminopropyl)silanetriol

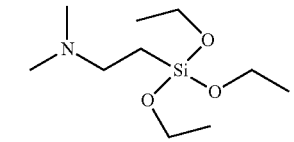

(2-Dimethylaminoethyl)triethoxysilane

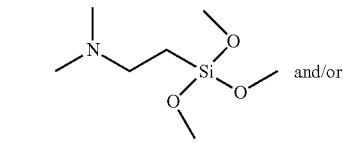

and/or (2-Dimethylaminoethyl)trimethoxysilane

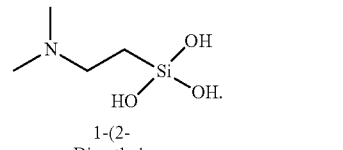

1-(2-Dimethylaminopropyl)silanetriol

The aforementioned organic silicon compound of formula (I) is commercially available.

(3-aminopropyl)trimethoxysilane, for example, can be purchased from Sigma-Aldrich®. (3-aminopropyl)triethoxysilane is also commercially available from Sigma-Aldrich®.

In a further embodiment, the product for the treatment of a keratinous material contains at least one organic silicon compound of formula (II)

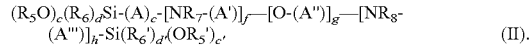

The organosilicon compounds of formula (II) each carry the silicon-containing groups $(R_5O)_c(R_6)_dSi$— and —$Si(R_6')_d(OR_5')_c$ at both ends.

In the central part of the molecule of formula (II) there are the groups -(A)$_e$- and —[NR$_7$-(A')]$_f$- and —[O-(A'')]$_g$- and —[NR$_8$-(A''')]$_h$-. Here, each of the radicals e, f, g and h can independently of one another stand for the number 0 or 1, with the proviso that at least one of the radicals e, f, g and h is different from 0. In other words, an organic silicon compound of formula (II) contains at least one grouping from the group including -(A)- and —[NR$_7$-(A')]- and —[O-(A'')]- and —[NR$_8$-(A''')]-.

In the two terminal structural units (R$_5$O)$_c$(R$_6$)$_d$Si— and —Si(R$_6$')$_{d'}$(OR$_5$')$_{c'}$, the radicals R5, R5', R5'' independently of one another represent a hydrogen atom or a C$_1$-C$_6$ alkyl group. The radicals R6, R6' and R6'' independently represent a C$_1$-C$_6$ alkyl group.

Here c stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

A very high anti-pollution effect of the product for the treatment of a keratinous material can be obtained if the radicals c and c' both stand for the number 3. In this case d and d' both stand for the number 0.

In a further preferred embodiment, the product for the treatment of a keratinous

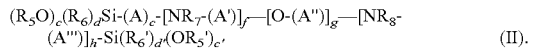
(R$_5$O)$_c$(R$_6$)$_d$Si-(A)$_e$-[NR$_7$-(A')]$_f$—[O-(A'')]$_g$—[NR$_8$-(A''')]$_h$-Si(R$_6$')$_{d'}$(OR$_5$')$_{c'}$, (II).

where
R$_5$ and R$_5$' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

(R$_5$O)$_3$Si-(A)$_e$-[NR$_7$-(A')]$_f$—[O-(A'')]$_g$—[NR$_8$-(A''')]$_h$—Si(OR$_5$')$_3$ (IIa).

The radicals e, f, g and h can independently stand for the number 0 or 1, whereby at least one radical from e, f, g and h is different from zero. The abbreviations e, f, g and h thus define which of the groupings -(A)$_e$- and —[NR$_7$-(A')]$_f$- and —[O-(A'')]$_g$- and —[NR$_8$-(A''')]$_h$- are located in the middle part of the organic silicon compound of formula (II).

In this context, the presence of certain groupings has proved to be particularly beneficial in terms of increasing the 'anti-pollution' effect. Particularly good results were obtained when at least two of the residues e, f, g and h stand for the number 1. Especially preferred e and f both stand for the number 1. Furthermore, g and h both stand for the number 0.

If e and f both stand for the number 1 and g and h both stand for the number 0, the organic silicon compounds correspond to formula (IIb)

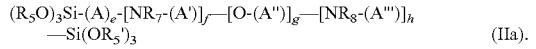
(R$_5$O)$_c$(R$_6$)$_d$Si-(A)-[NR$_7$-(A')]-Si(R$_6$')$_{d'}$(OR$_5$')$_{c'}$, (IIb).

The radicals A, A', A'', A''' and A'''' independently represent a linear or branched divalent C$_1$-C$_{20}$ alkylene group. Preferably the radicals A, A', A'', A''' and A'''' independently of one another represent a linear, divalent C$_1$-C$_{20}$ alkylene group. Further preferably the radicals A, A', A'', A''' and A'''' independently represent a linear divalent C$_1$-C$_6$ alkylene group. In particular, the radicals A, A', A'', A''' and A'''' independently of one another represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). In particular, the residues A, A', A'', A''' and A'''' stand for a propylene group (—CH$_2$—CH$_2$—CH$_2$—).

If the radical f represents the number 1, then the organic silicon compound of formula (II) contains a structural grouping —[NR$_7$-(A')]-.

If the radical h represents the number 1, then the organic silicon compound of formula (II) contains a structural grouping —[NR$_8$-(A''')]-.

Herein, the radicals R$_7$ and R$_8$ independently represent a hydrogen atom, a C$_1$-C$_6$ alkyl group, a hydroxy C$_1$-C$_6$-alkyl group, a C$_2$-C$_6$ alkenyl group, an amino-C$_1$-C$_6$-alkyl group or a grouping of the formula (III)

(A'''')-Si(R$_6$'')$_{d''}$(OR$_5$'')$_{c''}$ (III).

Very preferably, R$_7$ and R$_8$ independently represent a hydrogen atom, a methyl group, a 2-hydroxyethyl group, a 2-alkenyl group, a 2-aminoethyl group or a group of formula (III).

If the radical f represents the number 1 and the radical h represents the number 0, the organic silicon compound contains the grouping [NR$_7$-(A')] but not the grouping —[NR$_8$-(A''')]. If the radical R$_7$ now stands for a grouping of the formula (III), the product for the treatment of a keratinous material contains an organic silicone compound with 3 reactive silane groups.

In a further preferred embodiment, the product for the treatment of a keratinous material contains at least one organic silicon compound of formula (II)

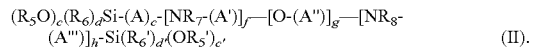
(R$_5$O)$_c$(R$_6$)$_d$Si-(A)$_e$-[NR$_7$-(A')]$_f$—[O-(A'')]$_g$—[NR$_8$-(A''')]$_h$-Si(R$_6$')$_{d'}$(OR$_5$')$_{c'}$ (II).

where
e and f both stand for the number 1,
g and h both stand for the number 0,
A and A' independently stand for a linear, divalent C$_1$-C$_6$-alkylene group and
R7 represents a hydrogen atom, a methyl group, a 2-hydroxyethyl group, a 2-alkenyl group, a 2-aminoethyl group or a group of formula (III).

In a further preferred embodiment, the product for the treatment of a keratinous material contains at least one organic silicon compound of formula (II), wherein
e and f both stand for the number 1,
g and h both stand for the number 0,
A and A' independently of one another represent a methylene group (—CH$_2$—), an ethylene group (—CH$_2$—CH$_2$—) or a propylene group (—CH$_2$—CH$_2$—CH$_2$),
and
R$_7$ represents a hydrogen atom, a methyl group, a 2-hydroxyethyl group, a 2-alkenyl group, a 2-aminoethyl group or a group of formula (III).

Organic silicon compounds of the formula (II) which are well suited for solving the problem are

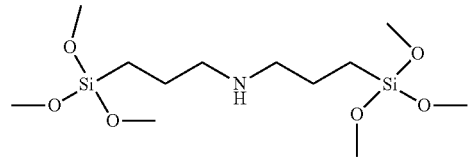

3-(trimethoxysilyl)-N-[3-trimethoxysilyl)propyl]-1-propanamine

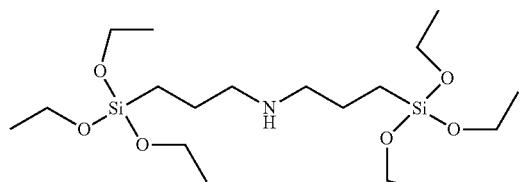

3-(Triethoxysilyl)-N-[3-triethoxysilyl)propyl]-1-propanamine

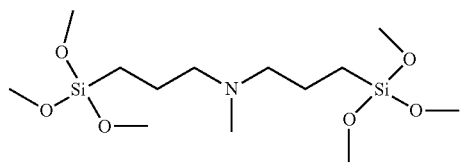

N-methyl-3-(trimethoxysilyl)-N-[3-trimethoxysilyl)propyl]-1-propanamine

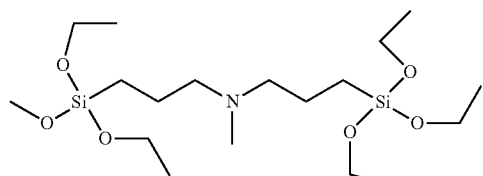

N-Methyl-3-(triethoxysilyl)-N-[3-triethoxysilyl)propyl]-1-propanamine

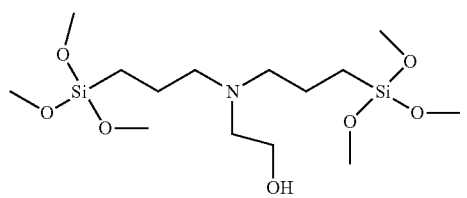

2-[Bis[3-(trimethoxysilyl)propyl]amino]-ethanol

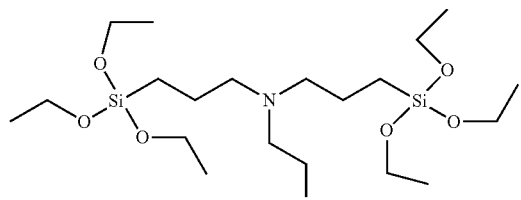

2-[bis[3-(triethoxysilyl)propyl]amino]ethanol

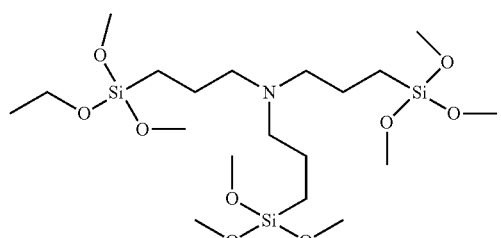

3-(Trimethoxysilyl)-N,N-bis[3-(trimethoxysilyl)propyl]-1-propanamine

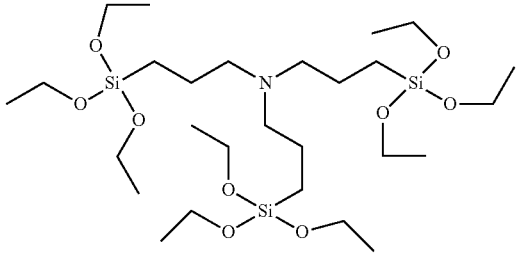

3-(Triethoxysilyl)-N,N-bis[3-(triethoxysilyl)propyl]-1-propanamine

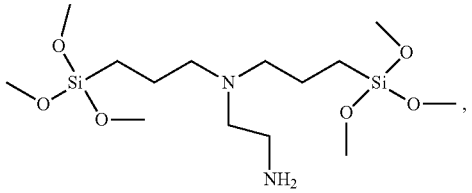

N1,N1-Bis[3-(trimethoxysilyl)propyl]-1,2-ethanediamine

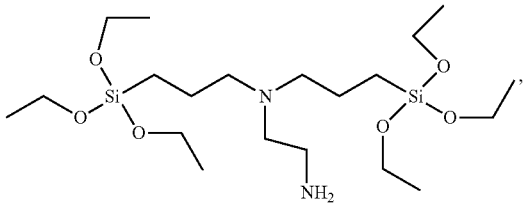

N1,N1-Bis[3-(triethoxysilyl)propyl]-1,2-ethanediamine

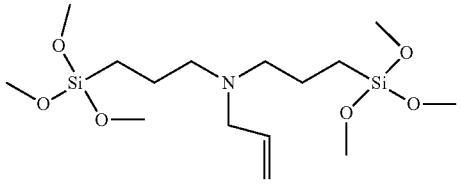

N,N-Bis[3-(trimethoxysilyl)propyl]-2-propen-1-amine

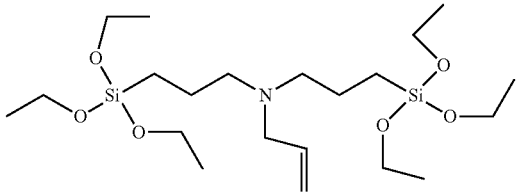

N,N-Bis[3-(triethoxysilyl)propyl]-2-propen-1-amine

The aforementioned organic silicon compounds of formula (II) are commercially available.

Bis(trimethoxysilylpropyl)amine with the CAS number 82985-35-1 can be purchased from Sigma-Aldrich®.

Bis[3-(triethoxysilyl)propyl]amine, also designated as 3-(Triethoxysilyl)-N-[3-(triethoxysilyl)propyl]-1-propanamine, with the CAS number 13497-18-2 is, for example, commercially available from Sigma-Aldrich® or can be commercially obtained from Evonik® under the product name Dynasylan® 1122.

N-methyl-3-(trimethoxysilyl)-N-[3-(trimethoxysilyl)propyl]-1-propanamine is alternatively referred to as bis(3-trimethoxysilylpropyl)-N-methylamine and can be purchased commercially from Sigma-Aldrich® or Fluorochem®.

3-(triethoxysilyl)-N,N-bis[3-(triethoxysilyl)propyl]-1-propanamine with the CAS number 18784-74-2 can be purchased for example from Fluorochem® or Sigma-Aldrich®.

It has also proved advantageous, if the product for the treatment of a keratinous material, used on the hair, contains at least one organic silicon compound of the formula (IV) $R_9Si(OR_{10})_k(R_{11})_m$ (IV).

The compounds of formula (IV) are organic silicon compounds selected from silanes having one, two or three silicon atoms, the organic silicon compound comprising one or more hydroxyl groups and/or hydrolysable groups per molecule.

The organic silicon compound(s) of formula (IV) may also be called a silane of the alkyl-alkoxy-silane or alkyl-hydroxy-silane type,

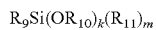   (IV), where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a further preferred embodiment, the product for the treatment of a keratinous material contains, in addition to the organic silicon compound(s) of formula (I), at least one more organic silicon compound of formula (IV)

   (IV), where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a similarly preferred embodiment, the product for the treatment of a keratinous material contains, in addition to the organic silicon compound(s) of formula (II), at least one more organic silicon compound of formula (IV)

   (IV), where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In a further preferred embodiment, the product for the treatment of a keratinous material contains, in addition to the organic silicon compound(s) of formula (I) and (II), at least one more organic silicon compound of formula (IV)

   (IV), where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

In the organic silicon compounds of formula (IV), the radical $R_9$ represents a $C_1$-$C_{12}$ alkyl group. This $C_1$-$C_{12}$ alkyl group is saturated and can be linear or branched. Preferably R9 stands for a linear $C_1$-$C_8$ alkyl group. Preferably $R_9$ stands for a methyl group, an ethyl group, an n-propyl group, an n-butyl group, an n-pentyl group, an n-hexyl group, an n-octyl group or an n-dodecyl group. Particularly preferred, $R_9$ stands for a methyl group, an ethyl group or an n-octyl group.

In the organic silicon compounds of formula (IV), the radical $R_{10}$ represents a hydrogen atom or a $C_1$-$C_6$ alkyl group. Especially preferably, $R_{10}$ stands for a methyl group or an ethyl group.

In the organic silicon compounds of formula (IV), the radical $R_{11}$ represents a $C_1$-$C_6$ alkyl group. Especially preferably, $R_{11}$ stands for a methyl group or an ethyl group.

Furthermore k stands for a whole number from 1 to 3, and m stands for the whole number 3-k. If k stands for the number 3, then m is equal to 0. If k stands for the number 2, then m is equal to 1. If k stands for the number 1, then m is equal to 2.

A very high anti-pollution effect can be achieved if the product for the treatment of a keratinous material contains at least one organic silicon compound of the formula (IV) in which the radical k stands for the number 3. In this case the residue m stands for the number 0.

Organic silicon compounds of the formula (IV) which are well suited for solving the problem are

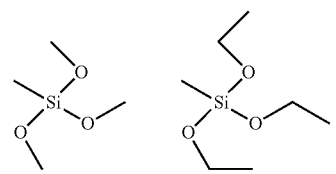

Methyltrimethoxysilane   Methyltriethoxysilane

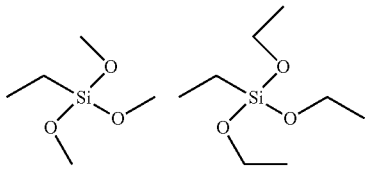

Ethyltrimethoxysilane   Ethyltriethoxysilane

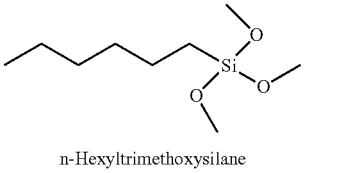

n-Hexyltrimethoxysilane

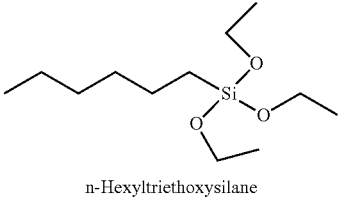

n-Hexyltriethoxysilane

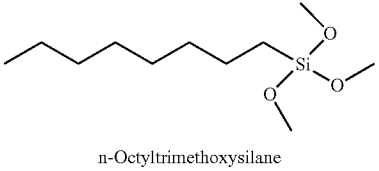

n-Octyltrimethoxysilane

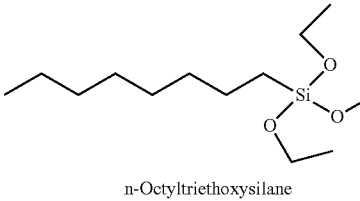

n-Octyltriethoxysilane

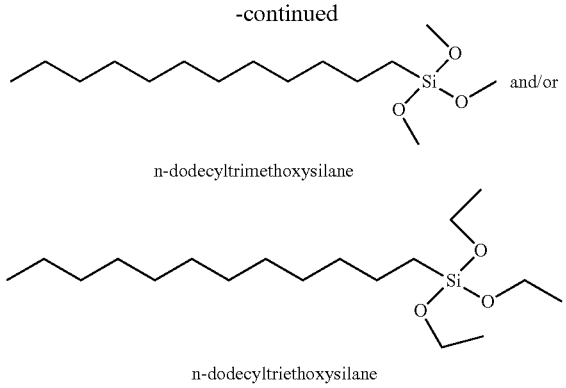

n-dodecyltrimethoxysilane n-dodecyltriethoxysilane as well as propyltrimelhoxysilane, propyltriethoxysilane, octadecyltrimethoxysilane and/or octadecyltrieihoxysilane.

The organic silicon compounds described above are reactive compounds.

It has been found that it is possible to maintain particularly sturdy and uniform films on the keratinous material, even if the product contains two structurally different organic silicon compounds, each of which contains one to three silicon atoms.

In a further preferred embodiment, a product is exemplified in that it contains at least one organic silicon compound of formula (I) and at least one organic silicon compound of formula (IV).

In an explicitly specifically preferred embodiment, a product is exemplified in that it contains at least one organic silicon compound of the formula (I), which is selected from the group including (3-Aminopropyl)triethoxysilane and (3-Aminopropyl)trimethoxysilane, and additionally contains at least one organic silicon compound of the formula (IV), which is selected from the group including methyltrimethoxysilane, methyltriethoxysilane, ethyltrimethoxysilane, ethyltriethoxysilane, propyltrimethoxysilane, propyltriethoxysilane, hexyltrimethoxysilane and hexyltriethoxysilane.

In a further preferred embodiment, a product is exemplified in that the product-based on the total weight of the product—contains:

From about 0.5 to about 5% by weight of at least one first organic silicon compound selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl) trimethoxysilane, (3-dimethylaminopropyl) triethoxysilane (2-dimethylaminoethyl) trimethoxysilane and (2-dimethylaminoethyl) triethoxysilane, and from about 3.2 to about 10.0% by weight of at least one second organic silicon compound selected from the group of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane and dodecyltriethoxysilane.

In the case of organic silicon components with at least one hydrolysable group, the addition of small quantities of water already leads to hydrolysis. The hydrolysis products and/or organic silicon compounds with at least one hydroxy group can react with each other in a condensation reaction. For this reason, the product can contain organosilicon compounds with at least one hydrolysable group as well as their hydrolysis and/or condensation products. When using organosilicon compounds with at least one hydroxyl group, the product can contain organic silicon compounds with at least one hydroxyl group as well as their condensation products.

A condensation product is understood to mean a product that is created due to the reaction of at least two organic silicon compounds each with at least one hydroxyl group or hydrolysable group per molecule on elimination of water and/or elimination of an alkanol. The condensation products can, for example, be dimers, or even trimers or oligomers, where in the condensation products are always in balance with the monomers. Depending on the water quantity added or consumed in the hydrolysis, the balance shifts from monomeric organic silicon compounds to condensation product.

In the context of the present disclosure, specifications in weight %—unless otherwise specified—always in relation to the total weight of the cosmetic product.

As the second component essential for the present disclosure, the cosmetic product for the treatment of a keratinous material contains at least one polyacrylate copolymer, which is formed from the monomer acrylic acid and acrylamidopropyltrimonium chloride. The at least one polyacrylate copolymer is thus formed from the following monomers:

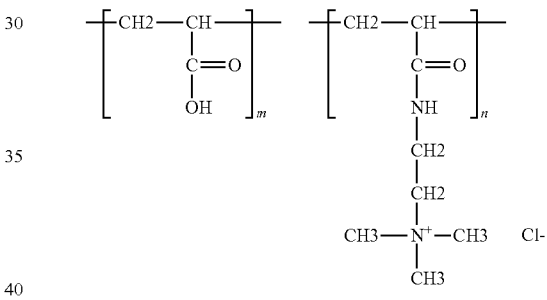

In which m and n stand for the number of co-monomers in the polymer, wherein the ratio of m to n lies between from about 90 to about 10 up to about 10 to about 90, preferably between from about 75 to about 25 up to about 25 to about 75, more preferably between from about 60 to about 40 and about 40 to about 60.

The polyacrylate copolymer comprises, according to a preferred embodiment of the present disclosure, other monomer units different from these monomers.

In the course of the work leading to the present disclosure, it has been found that it is advantageous for achieving advantageous properties regarding the washout protection of colored hair with a structure protection at the same time, if the organic silicon compounds, especially 3-(triethoxysilyl)-N-[3-(triethoxysilyl)propyl]-1-propanamine i.e. a Bis(triethoxysilylpropyl)amine, and/or (3-Aminopropyl)triethoxysilane i.e. an aminopropyltriethoxysilane (AMEO), is combined with the polyacrylate copolymer.

A particularly preferred product that can be used as a mandatory component is the product W 37194 from the company Giovanni Bozzetto S.p. The polyacrylate copolymer is known under the INCI designation Acrylamidopropyltrimonium chloride/Acrylates copolymer.

The combination of the organic silicon compound that contains one to three silicon atoms, with the polyacrylate copolymer forms a layer on the hair. This ensures that the hair is hydrophobized, which leads to a reduction in the frizz. This also improves the washout protection of colored hair.

According to a preferred embodiment of the present disclosure, the quantity of the polyacrylate copolymer in the cosmetic product is from about 0.01 to about 10 weight %, preferably from about 0.25 to about 8 weight %, more preferably from about 0.5 to about 6 weight % based on the total weight of the cosmetic product.

Other components of the hair treatment product shall be described hereafter, which can be contained in the products besides the above-described mandatory and optional ingredients.

It can be preferable that the product for the treatment of a keratinous material further comprise from about 0.001 to about 20 weight % of at least one quaternary compound. This holds especially for agents that lend care properties to the keratinous material.

It is preferred that the at least one quaternary compound be selected from at least one of the groups including:
i) the monoalkyl quats and/or
ii) the ester quats and/or
iii) the quaternary imidazoline of the formula (Tkat2).

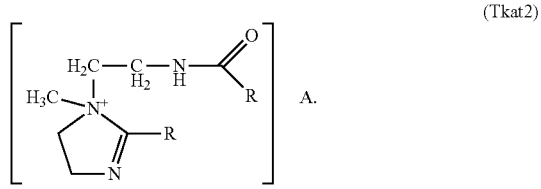

(Tkat2)

In which the radical R independently stands for a saturated or unsaturated, linear or branched hydrocarbon radical with a chain length from about 8 to about 30 carbon atoms and A stands for a physiologically compatible anion, and/or
iv) the amidoamines and/or cationized amidoamines and/or
v) quaternized cellulose derivatives, especially polyquaternium 10, polyquaternium-24, polyquaternium-27, polyquaternium-67, polyquaterium-72 and/or
vi) Cationic alkyl polyglycosides and/or
vii) Cationized honey and/or
viii) Cationic guar derivatives and/or
ix) Chitosan and/or
x) quaternized polyvinyl alcohol,
and mixtures thereof.

Furthermore, the cosmetic product can contain firming compounds, preferably selected from the group including waxes and/or other synthetic polymers. That means, waxes and/or other synthetic polymers can be added as firming compounds as a supplement. Ideally, the polysaccharides and other firming compounds, when used on the keratinous material, leave a polymer film that lends a strong hold to the hairstyle on the one hand, is however sufficiently flexible on the other, so that it does not break on being stressed.

For example, polycarboxylic acids can be used in the cosmetic product as film formers. They settle on the hair and establish a temporary plasticity of the hair. The film former can be a homopolymer or copolymer derived from itaconic acid. If the film former is present exclusively in the form of polymerized itaconic acid and/or a salt of the itaconic acid, the film former forms a homopolymer. An example of such a polymer is PVP/VA/itaconic acid copolymer (INCI).

The other synthetic polymers can be divided in cationic, anionic, nonionic and amphoteric firming polymers.

Suitable synthetic polymers comprise, for example, polymers with the following INCI designation. Acrylamide/ Ammonium Acrylate Copolymer, Acrylamides/DMAPA Acrylates/Methoxy PEG Methacrylate Copolymer, Acrylamidopropyltrimonium Chloride/Acrylamide Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide/Diphenyl Amodimethicone Copolymer, Acrylates/Stearyl Acrylate/ Ethylamine Oxide Methacrylate Copolymer, Acrylates/VA Copolymer, Acrylates/Hydroxyesters Acrylates Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/ Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, Bacillus/Rice Bran Extract/Soybean Extract Ferment Filtrate, Bis-Butyloxyamodimethicone/PEG-60 Copolymer, Butyl Acrylate/ Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/ MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/ Acrylates Copolymer, PEG/PPG-25/25 Dimethicone/ Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer. Cellulose ethers, such as hydroxypropylcellulose, hydroxyethylcellulose and methylhydroxypropylcellulose are also suitable.

Preferably, the firming compound comprises a vinylpyrrolidone-containing polymer. Particularly preferably, the firming compound comprises a polymer selected from the group including polyvinylpyrrolidone (PVP), vinylpyrrolidone-vinylacetate-copolymer (VP/VA copolymer), vinyl caprolactam/VP/dimethylaminoethyl methacrylate copolymer (INCI), VP/DMAPA acrylates copolymer (INCI) and mixtures thereof.

Accordingly, it is particularly preferable that the firming compound comprises a synthetic polymer selected from the group including polyvinylpyrrolidone (PVP), vinylpyrrolidone-vinylacetate-copolymer (VP/VA copolymer), vinyl caprolactam/VP/dimethylaminoethyl methacrylate copolymer (INCI), VP/DMAPA acrylates copolymer (INCI), octylacrylamide/acrylates/butylaminoethyl methacrylate copolymer (INCI) and mixtures thereof.

Furthermore, the cosmetic product can contain an Octylacrylamide/Acrylates/Butylaminoethyl Methacrylate Copolymer (INCI) as a firming polymer. This copolymer is sold by Akzo Nobel® under the names "Amphomer®", "Amphomer® HC", "Amphomer® 4961", "Amphomer® EDGE" and "Amphomer® LV 71" in various modifications.

Furthermore, in preferred embodiment, the cosmetic product can contain polysaccharides. According to some embodiments, the preferably contained polysaccharides are starch, thermally and/or mechanically treated starch, oxidatively, hydrolytically or oxidized enzymatically broken down starches, oxidized hydrolytically or oxidized enzymatically broken down starches as well as chemically modified starches. In this context, all starches are generally suitable. According to some embodiments, these can be for example, but not restricted to, starch from corn, wheat, rice, peas, barley, rye, cassava, tapioca, sweet potatoes or potatoes. In some embodiment, for example, native starches are preferably used. The designation native starch refers to the starch that is accessed from natural sources, such as the above-mentioned ones. A native starch is a common commercial product and is, therefore, easily available.

According to an embodiment, the polysaccharide is corn, wheat, rice, pea, barley, rye, cassava, tapioca, sweet potato or potato starch. According to an embodiment, the polysaccharide is the corresponding native starch of the above type. Mixtures of the above are also suitable. According to an embodiment, the polysaccharide is preferably corn starch, especially native corn starch. The most preferred one is the corn starch Collamyl 8412 of the company Agrabne Wien.

In order to cope with the different requirements for the product for the treatment of a keratinous material in the form of one agent for temporary shaping of a keratinous material (=Styling material), a multitude of synthetic polymers have already been developed as firming compounds, which can be used in a product for the treatment of a keratinous material.

The product for the treatment of a keratinous material can comprise especially an agent for temporarily shaping a keratinous material, an agent for cleaning a keratinous material, an agent for care of a keratinous material, an agent for care and/or an agent for care and cleaning of a keratinous material.

The cosmetic composition can, additionally or alternatively to a synthetic polymer, contain at least one natural or synthetic wax, which has a melting point above about 37° C., as a firming compound.

As natural or synthetic waxes, solid paraffins or isoparaffins, vegetable waxes such as candelila wax, carnauba wax, esparto grass wax, Japan wax, cork wax, sugar cane wax, ouricury wax, montan wax, sunflower wax, fruit waxes and animal waxes such as beeswaxes and other insect waxes, whale wax, shellac wax, wool wax and brushing grease, furthermore mineral waxes such as Ceresin and Ozokerite or the petrochemical waxes such as petrolatum, paraffin wax, microwaxes from polyethylene or polypropylene and polyethylene glycol waxes can be used. It can be advantageous to use hydrated or hardened waxes. Furthermore, chemically modified waxes, especially resin waxes, for example montan ester waxes, sasol waxes and hydrated jojoba waxes can also be used.

Furthermore, the triglycerides of saturated and, in some cases, hydroxylized about C 16-30 fatty acids, such as hardened triglyceride fats (hydrated palm oil, hydrated coconut oil, hydrated castor oil), glyceryl tribehenate or glyceryl tri-12 hydroxy stearate, are suitable.

The wax components can also be selected from the group of esters from saturated, unbranched alkane carboxylic acids of a chain length of from about 22 to about 24 C atoms and saturated, unbranched alcohols of a chain length of from about 22 to about 24 C atoms, if the wax components or the totality of the wax components are solid at room temperature. Silicone waxes, such as stearyltrimethylsilane/stearyl alcohol can also be advantageous.

Natural, chemically modified, and synthetic waxes can be used alone or in combination. Thus, even several waxes can be used. Moreover, a series of wax mixes, possibly in mixture with other additives, is also commercially available. Examples of usable mixtures are the ones available under the names "Special wax 7686 OE' (a mixture of cetyl palmitate, bees wax, micro crystalline wax and polyethylene with a melting range of about 73-75° C., manufacturer: Kahl® & Co), Plywax® GP 200 (a mixture of stearyl alcohol and polyethylene glycol stearate with melting point of about 47-51° C.; manufacturer: Croda®) and "Weichceresin® FL 400" (a vaseline/vaseline oil/wax mixture with a melting point of about 50-54° C.; manufacturer: Parafluid Mineralölgesellschaft).

The wax selected from Carnauba wax (INCI: Copernicia Cerifera Cera) bees wax (INCI: Beeswax), Petrolatum (INCI), micro crystalline wax and especially mixtures therefrom are preferred.

Preferred mixtures comprise the combination of Carnauba wax (INCI: Copernicia Cerifera Cera), Petrolatum and micro crystalline wax or the combination of bees wax (INCI: Beeswax) and Petrolatum.

The wax or the wax components should be solid at about 25° C. and should melt in the range of >about 37° C.

The product for the treatment of a keratinous material contains a firming compound preferably in a total quantity of from about 0.5 to about 50 weight %, preferably from about 1 to about 40 weight %, more preferred from about 1.5 to about 30 weight %, still more preferred from about 2 to about 25 weight %, based on the total weight of the cosmetic composition.

Other suitable ingredients comprise nonionic polymers, anionic polymers, (other) cationic polymers, waxes, protein hydrolysates, amino acids, oligopeptides, vitamins, provitamins, vitamin precursors, betaines, biochinones, purine (derivatives), care substances, plant extracts, silicones, ester oils, UV light protection filters, thickeners, electrolytes, pH adjusters, swelling agents, dyes, anti-dandruff agents, complexing agents, opacifiers, pearlizing agents, pigments, stabilizers, propellants, anti-oxidants, perfume oils and/or preservatives.

In the preferred embodiments 1 to 48, the preferred organic silicon compounds with the preferred polyacrylate copolymers are combined with each other in a cosmetic product as listed below. In preferred embodiments of the present disclosure, the cosmetic products contain the following combinations with other ingredients mentioned above.

|    | Silane compound | Other ingredients |
| --- | --- | --- |
| 1 | (3-Aminopropyl)trimethoxysilane | Acrylamidopropyltrimonium Chloride/Acrylates Copolymer |
| 2 | (3-Aminopropyl)triethoxysilane | Acrylamidopropyltrimonium Chloride/Acrylates Copolymer |
| 3 | (2-Aminoethyl)trimethoxysilane | Acrylamidopropyltrimonium Chloride/Acrylates Copolymer |
| 4 | (2-Aminoethyl)triethoxysilane | Acrylamidopropyltrimonium Chloride/Acrylates Copolymer |
| 5 | (3-Dimethylaminopropyl)trimethoxysilane | Acrylamidopropyltrimonium Chloride/Acrylates Copolymer |
| 6 | (3-Dimethylaminopropyl)triethoxysilane | Acrylamidopropyltrimonium Chloride/Acrylates Copolymer |
| 7 | (2-Dimethylaminoethyl)trimethoxysilane | Acrylamidopropyltrimonium Chloride/Acrylates Copolymer |
| 8 | (2-Dimethylaminoethyl)triethoxysilane | Acrylamidopropyltrimonium Chloride/Acrylates Copolymer |
| 9 | 3-(Trimethoxysilyl)-N-[3-(trimethoxysilyl)propyl]-1-propanamine | Acrylamidopropyltrimonium Chloride/Acrylates Copolymer |
| 10 | 3-(Triethoxysilyl)-N-[3-(triethoxysilyl)propyl]-1-propanamine | Acrylamidopropyltrimonium Chloride/Acrylates Copolymer |
| 11 | N-Methyl-3-(trimethoxysilyl)-N-[3-(trimethoxysilyl)propyl]-1-propanamine | Acrylamidopropyltrimonium Chloride/Acrylates Copolymer |
| 12 | N-Methyl-3-(triethoxysilyl)-N-[3-(triethoxysilyl)propyl]-1-propanamine | Acrylamidopropyltrimonium Chloride/Acrylates Copolymer |
| 13 | 2-[Bis[3-(trimethoxysilyl) propyl]amino]-ethanol | Acrylamidopropyltrimonium Chloride/Acrylates Copolymer |
| 14 | 2-[Bis[3-(triethoxysilyl) propyl]amino]-ethanol | Acrylamidopropyltrimonium Chloride/Acrylates Copolymer |
| 15 | 3-(Trimethoxysilyl)-N,N-bis[3-(trimethoxysilyl)propyl]-1-propanamine | Acrylamidopropyltrimonium Chloride/Acrylates Copolymer |
| 16 | 3-(Triethoxysilyl)-N,N-bis[3-(triethoxysilyl)propyl]-1-propanamine | Acrylamidopropyltrimonium Chloride/Acrylates Copolymer |
| 17 | N1,N1-Bis[3-(trimethoxysilyl)propyl]-1,2-ethane diamine | Acrylamidopropyltrimonium Chloride/Acrylates Copolymer |
| 18 | N1,N1-Bis[3-(triethoxysilyl)propyl]-1,2-ethane diamine | Acrylamidopropyltrimonium Chloride/Acrylates Copolymer |
| 19 | N,N-Bis[3-(trimethoxysilyl)propyl]-2-propene-1-amine | Acrylamidopropyltrimonium Chloride/Acrylates Copolymer |
| 20 | N,N-Bis[3-(triethoxysilyl)propyl]-2-propene-1-amine | Acrylamidopropyltrimonium Chloride/Acrylates Copolymer |
| 21 | Methyltrimethoxysilane | Acrylamidopropyltrimonium Chloride/Acrylates Copolymer |
| 22 | Methyltriethoxysilane | Acrylamidopropyltrimonium Chloride/Acrylates Copolymer |
| 23 | Ethyltrimethoxysilane | Acrylamidopropyltrimonium Chloride/Acrylates Copolymer |
| 24 | Ethyltriethoxysilane | Acrylamidopropyltrimonium Chloride/Acrylates Copolymer |
| 25 | Octyltrimethoxysilane | Acrylamidopropyltrimonium Chloride/Acrylates Copolymer |
| 26 | Octyltriethoxysilane | Acrylamidopropyltrimonium Chloride/Acrylates Copolymer |
| 27 | Dodecyltrimethoxysilane | Acrylamidopropyltrimonium Chloride/Acrylates Copolymer |

| | Silane compound | Other ingredients |
|---|---|---|
| 28 | Dodecyltriethoxysilane | Acrylamidopropyltrimonium Chloride/Acrylates Copolymer |
| 29 | Propyltrimethoxysilane | Acrylamidopropyltrimonium Chloride/Acrylates Copolymer |
| 30 | Propyltriethoxysilane | Acrylamidopropyltrimonium Chloride/Acrylates Copolymer |
| 31 | Hexyltrimethoxysilane | Acrylamidopropyltrimonium Chloride/Acrylates Copolymer |
| 32 | Hexyltriethoxysilane | Acrylamidopropyltrimonium Chloride/Acrylates Copolymer |
| 33 | Octadecyltrimethoxysilane | Acrylamidopropyltrimonium Chloride/Acrylates Copolymer |
| 34 | Octadecyltriethoxysilane | Acrylamidopropyltrimonium Chloride/Acrylates Copolymer |
| 35 | (3-Aminopropyl)triethoxysilane + methyltrimethoxysilane | Acrylamidopropyltrimonium Chloride/Acrylates Copolymer |
| 36 | (3-Aminopropyl)triethoxysilane + Methyltriethoxysilane | Acrylamidopropyltrimonium Chloride/Acrylates Copolymer |
| 37 | (3-Aminopropyl)triethoxysilane + ethyltrimethoxysilane | Acrylamidopropyltrimonium Chloride/Acrylates Copolymer |
| 38 | (3-Aminopropyl)triethoxysilane + ethyltriethoxysilane | Acrylamidopropyltrimonium Chloride/Acrylates Copolymer |
| 39 | (3-Aminopropyl)triethoxysilane + propyltrimethoxysilane | Acrylamidopropyltrimonium Chloride/Acrylates Copolymer |
| 40 | (3-Aminopropyl)triethoxysilane + propyltriethoxysilane | Acrylamidopropyltrimonium Chloride/Acrylates Copolymer |
| 41 | (3-Aminopropyl)triethoxysilane + hexyltrimethoxysilane | Acrylamidopropyltrimonium Chloride/Acrylates Copolymer |
| 42 | (3-Aminopropyl)triethoxysilane + hexyltriethoxysilane | Acrylamidopropyltrimonium Chloride/Acrylates Copolymer |
| 43 | (3-Aminopropyl)triethoxysilane + octyltrimethoxysilane | Acrylamidopropyltrimonium Chloride/Acrylates Copolymer |
| 44 | (3-Aminopropyl)triethoxysilane + octyltriethoxysilane | Acrylamidopropyltrimonium Chloride/Acrylates Copolymer |
| 45 | (3-Aminopropyl)triethoxysilane + dodecyltrimethoxysilane | Acrylamidopropyltrimonium Chloride/Acrylates Copolymer |
| 46 | (3-Aminopropyl)triethoxysilane + dodecyltriethoxysilane | Acrylamidopropyltrimonium Chloride/Acrylates Copolymer |
| 47 | (3-Aminopropyl)triethoxysilane + octadecyltrimethoxysilane | Acrylamidopropyltrimonium Chloride/Acrylates Copolymer |
| 48 | (3-Aminopropyl)triethoxysilane + octadecyltriethoxysilane | Acrylamidopropyltrimonium Chloride/Acrylates Copolymer |

The product for the treatment of a keratinous material can already contain the combination of the active ingredients of at least one organic silicon compound and the polyacrylate copolymer. In this embodiment, the product for the treatment of a keratinous material is already sold in ready-to-use form. In order to provide a formulation that is as stable as possible during storage, the product itself is preferably packaged with low or no water.

Alternatively, the at least one organic silicon compound is added to a base comprising all ingredients of the product for the treatment of a keratinous material with the exception of the at least one organic silicon compound, where the organic silicon compound is added a maximum about 12 hours, preferably a maximum of about 6 hours, more preferably a maximum of about 3 hours, even more preferably a maximum of about 1 hour before using the product for the treatment of a keratinous material.

Furthermore, alternatively, the organic silicon compound is added to a cosmetic product just shortly before use, i.e., from about 1 minute to about 12 hours, preferably from about 2 minutes to about 6 hours, especially preferably from about 1 minute to about 3 hours, most especially preferably from about 1 minute to about 1 hour.

In another alternative, the organic silicon compound is added to an aqueous solution, which is applied to the hair and in the second step, an aqueous solution or a cosmetic product, which contains polyacrylate copolymer, is applied to the hair.

The user can for example stir or shake an agent (α), which contains the organic silicon compound(s), first with an agent (β), which comprises the remaining ingredients of the product for the treatment of a keratinous material. The user can now apply this mixture of (α) and (β) to the keratinous materials—either directly after their production or after a short reaction time of about 1 minute to about 20 minutes. The agent (β) can contain water, especially water in a quantity >about 30 weight %, based on the total weight of the product for the treatment of keratinous materials.

Another object of the present application is the use of a cosmetic product for the treatment of a keratinous material, for the washout protection of colored keratinous material, for shaping of the surface of keratinous material and/or for care of keratinous material.

Regarding other preferred embodiments of the use, what was said about the cosmetic product is applicable mutatis mutandis.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for the treatment of a keratinous material, comprising
a) at least one organic silicon compound that comprises one to three silicon atoms, wherein the at least one organic silicon compound comprises a compound of a formula (I) and a compound of a formula (IV),
wherein in the organic silicon compound of formula (I)

$$R_1R_2N\text{-}L\text{-}Si(OR_3)_a(R_4)_b \quad (I),$$

$R_1$, $R_2$ both represent a hydrogen atom,
L represents a linear, divalent $C_1$-$C_6$-alkylene group,
$R_3$, $R_4$ independently represent a methyl group or an ethyl group,
a stands for the number 3 and
b stands for the number 0 and
wherein in the organic silicon compound of formula (IV)

$$R_9Si(OR_{10})_k(R_{11})_m \quad (IV),$$

$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k; and
b) at least one polyacrylate copolymer that is formed from the monomers acrylic acid and acrylamidopropyltrimonium chloride.

2. The cosmetic product for the treatment of a keratinous material as claimed in claim 1,
wherein the at least one organic silicon compound further comprises a compound of a formula (II)
wherein in the organic silicon compound of formula (II)

$$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_{6'})_{d'}(OR_{5'})_{c'} \quad (II),$$

$R_5$, $R_{5'}$, $R_{5''}$, $R_6$, $R_{6'}$ and $R_{6''}$ independently represent a $C_1$-$C_6$ alkyl group,
A, A', A", A''' and A'''' independently represent a linear or branched, divalent $C_1$-$C_{20}$-alkylene group,
$R_7$ and $R_8$ independently represent a hydrogen atom, a $C_1$-$C_6$-alkyl group, a hydroxy-$C_1$-$C_6$-alkyl group, a $C_2$-$C_6$-alkenyl group, an amino-$C_1$-$C_6$-alkyl group or a grouping of the formula (III)

$$(A'''')\text{-}Si(R_{6''})_{d''}(OR_{5''})_{c''} \quad (III),$$

wherein c stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
with the proviso that at least one of the radicals from e, f, g and h is different from 0.

3. The cosmetic product for the treatment of a keratinous material as claimed in claim 1,
wherein
the organic silicon compound of the formula (I) is selected from the group of
(3-Aminopropyl)trimethoxysilane
(3-Aminopropyl)triethoxysilane
(2-Aminoethyl)trimethoxysilane and
(2-Aminoethyl)triethoxysilane.

4. The cosmetic product for the treatment of a keratinous material as claimed in claim 1, wherein the cosmetic product comprises the organic silicon compound of the formula (I) in a quantity of from about 0.01 to about 10 weight %, based on a total weight of the cosmetic product.

5. The cosmetic product for the treatment of a keratinous material as claimed in claim 1, wherein the compound of the formula (IV)
is selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane
Dodecyltriethoxysilane
Octadecyltrimethoxysilane and
Octadecyltriethoxysilane.

6. The cosmetic product for the treatment of a keratinous material as claimed in claim 1, wherein the polyacrylate copolymer is formed from the following monomers:

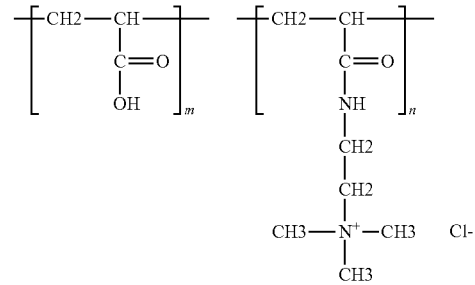

where n and m represent the number of monomer units, wherein the ratio of m to n lies between from about 90 to about 10 up to from about 10 to about 90.

7. The cosmetic product for the treatment of a keratinous material as claimed in claim 1, wherein the cosmetic product comprises the polyacrylate copolymer in a quantity of from about 0.01 to about 10 weight %, based on a total weight of the cosmetic product.

8. The cosmetic product for the treatment of a keratinous material as claimed in claim 1, wherein the cosmetic product further comprises a component c), wherein the component c) is selected from the group of glycerin, urea, hyaluronic acid, silanol ester of the hyaluronic acid, panthenol, taurine, ceramides, phytosteroles, aloe vera extracts, creatine, creatinine, sodium hyaluronate, polysaccharides, biosaccharides gum-1, cucumber extracts, butylene glycol, propylene glycol, methyl propanediol, ethylhexylglycerin, sorbitol, amino acids, amino acid derivatives, lactic acid, lactates, ethylhexyloxyglycerin, and combinations thereof.

9. The cosmetic product for the treatment of a keratinous material as claimed in claim 1, wherein the the compound of formula (I) comprises aminopropyltriethoxysilane, and the compound of formula (II) comprises methyltriethoxysilane.

10. The cosmetic product for the treatment of a keratinous material as claimed in claim 1, wherein the cosmetic product for the treatment of a keratinous material comprises:
from about 0.5 to about 5 weight % of the compound selected from the group of (3-Aminopropyl)trimethoxysilane, (3-Aminopropyl)triethoxysilane, (2-Aminoethyl)trimethoxysilane, (2-Aminoethyl)triethoxysilane, and combinations thereof, and
from about 3.2 to about 10.0% by weight of the compound of the formula (IV) selected from the group of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane, and octadecyltriethoxysilane.

11. A method for treating keratinous material, the method comprising the steps of:
applying a cosmetic product to the keratinous material, wherein the cosmetic product comprises an organic silicon compound, wherein the organic silicon compound comprises one to three silicon atoms, and a polyacrylate copolymer formed from the monomers acrylic acid and acrylamidopropyltrimonium chloride, and wherein the organic silicon compound comprises a compound of a formula (I) and a compound of a formula (IV),
wherein in the organic silicon compound of formula (I)

$R_1R_2N-L-Si(OR_3)_a(R_4)_b$ (I), $R_1$, $R_2$ both represent a hydrogen atom,
L represents a linear, divalent $C_1$-$C_6$-alkylene group,
$R_3$, $R_4$ independently represent a methyl group or an ethyl group,
a stands for the number 3 and
b stands for the number 0 and
wherein in the organic silicon compound of formula (IV)

$R_9Si(OR_{10})_k(R_{11})_m$ (IV), $R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3-k.

12. The cosmetic product for the treatment of a keratinous material as claimed in claim 2, wherein:
the organic silicon compound of the formula (II) is selected from the group of:
3-(trimethoxysilyl)-N-[3-(trimethoxysilyl)propyl]-1-propanamine,
3-(Triethoxysilyl)-N-[3-(triethoxysilyl)propyl]-1-propanamine,
N-methyl-3-(trimethoxysilyl)-N-[3-(trimethoxysilyl)propyl]-1-propanamine,
N-Methyl-3-(triethoxysilyl)-N-[3-(triethoxysilyl)propyl]-1-propanamine,
2-[Bis[3-(trimethoxysilyl)propyl]amino]-ethanol,
2-[bis[3-(triethoxysilyl)propyl]amino]ethanol,
3-(Trimethoxysilyl)-N,N-bis[3-(trimethoxysilyl)propyl]-1-propanamine,
3-(Triethoxysilyl)-N,N-bis[3-(triethoxysilyl)propyl]-1-propanamine,
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propene-1-amine, and/or
N,N-bis[3-(triethoxysilyl)propyl]-2-propen-1-amine.

13. The cosmetic product for the treatment of a keratinous material as claimed in claim 1, wherein:
the organic silicon compound of formula (I) is (3-aminopropyl)triethoxysilane.

14. The cosmetic product for the treatment of a keratinous material as claimed in claim 2, wherein:
the organic silicon compound of the formula (II) is 3-(triethoxysilyl)-N-[3-(triethoxysilyl)propyl]-1-propanamine.

15. The cosmetic product for the treatment of a keratinous material as claimed in claim 2, wherein the cosmetic product is free of water.

16. The cosmetic product for the treatment of a keratinous material as claimed in claim 2, wherein the cosmetic product comprises the organic silicon compound of the formula (II) in a quantity of from about 0.01 to about 10 weight %, based on a total weight of the cosmetic product.

17. The cosmetic product for the treatment of a keratinous material as claimed in claim 2, wherein the cosmetic product comprises the organic silicon compound of the formula (II) in a quantity of from about 0.1 to about 6 weight %, based on a total weight of the cosmetic product.

18. The cosmetic product for the treatment of a keratinous material as claimed in claim 1, wherein the cosmetic product comprises the organic silicon compound of the formula (I) in a quantity of from about 0.1 to about 4 weight %, based on a total weight of the cosmetic product.

19. The cosmetic product for the treatment of a keratinous material as claimed in claim 1, wherein the compound of the formula (I) consists of aminopropyltriethoxysilane, and the compound of the formula (IV) consists of methyltriethoxysilane.

20. The cosmetic product for the treatment of a keratinous material as claimed in claim 1, wherein the cosmetic product comprises the polyacrylate copolymer in a quantity of from about 0.5 to about 6 weight %, based on a total weight of the cosmetic product.

* * * * *